US011311565B2

(12) United States Patent
Samant et al.

(10) Patent No.: US 11,311,565 B2
(45) Date of Patent: Apr. 26, 2022

(54) SYNERGISTIC NUTRITIONAL COMPOSITIONS FOR PROMOTING AXONAL REGENERATION

(71) Applicant: CELAGENEX RESEARCH (INDIA) PVT. LTD., Maharashtra (IN)

(72) Inventors: Rajaram Samant, Thane-West (IN); Rajendra Prasad Tongra, Jaipur (IN)

(73) Assignee: CELAGENEX RESEARCH (INDIA) PVT. LTD., Thane (IN)

( * ) Notice: Subject to any disclaimer, the term of this patent is extended or adjusted under 35 U.S.C. 154(b) by 0 days.

(21) Appl. No.: 17/359,482

(22) Filed: Jun. 25, 2021

(65) Prior Publication Data
US 2021/0401866 A1    Dec. 30, 2021

(30) Foreign Application Priority Data

Jun. 25, 2020  (IN) .............................. 202021027004

(51) Int. Cl.
A61K 31/7068    (2006.01)
A61K 31/155     (2006.01)
A23L 29/00      (2016.01)
A23L 33/00      (2016.01)
A61K 9/00       (2006.01)
A61P 25/00      (2006.01)

(52) U.S. Cl.
CPC ........ A61K 31/7068 (2013.01); A23L 29/045 (2016.08); A23L 33/30 (2016.08); A61K 9/0053 (2013.01); A61K 31/155 (2013.01); A61P 25/00 (2018.01)

(58) Field of Classification Search
None
See application file for complete search history.

(56) References Cited

U.S. PATENT DOCUMENTS

| | | | |
|---|---|---|---|
| 8,912,144 B2 | 12/2014 | Benowitz | |
| 2010/0172890 A1* | 7/2010 | Gilad | ..................... A61K 45/06 424/94.1 |
| 2011/0071088 A1* | 3/2011 | Benowitz | ........... A61K 31/7076 514/17.8 |
| 2015/0182479 A1* | 7/2015 | Glynn | .................... A61K 45/06 514/634 |

FOREIGN PATENT DOCUMENTS

| | | |
|---|---|---|
| EP | 1009412 B1 | 6/2000 |
| EP | 1624894 A4 | 2/2006 |
| WO | 98/13037 A1 | 4/1998 |
| WO | 2014096958 A | 6/2014 |
| WO | WO-2017174322 A1 * 10/2017 | ............. A23L 27/23 |

OTHER PUBLICATIONS

Li et al., "Exploring Optic Nerve Axon Regeneration", Curr Neuropharmacol. Aug. 2017; 15(6): 861-873.
H.P. Hatten Jr. M.D. "Dysmyelinating leukodystrophies: "LACK Proper Myelin"", Pediatr Radiol 21, 477-482 (Nov. 1991).
Huebner et al., "Axon regeneration in the peripheral and central nervous systems", Results Probl Cell Differ. Jan. 1, 2009; 48: 339-351.
Coleman and Freeman, "Wallerian degeneration, wld(s), and nmnat", Annu. Rev. Neurosci. Jan. 10, 2010. 33:245-67.
Wu et al., "Promoting axonal myelination for improving neurological recovery in spinal cord injury", J Neurotrauma. Oct. 2009;26(10):1847-56.
Lu et al., "Advances in secondary spinal cord injury: role of apoptosis", Spine (Phila Pa 1976). Jul. 15, 2000; 25(14):1859-66.
Raul A. Marinelli, "Molecular mechanisms of water transport in bile formation: aquaporin water channels", TRENDS in Molecular Medicine vol. 10 No. 12 ;2004.
Alizadeh et al., "Microenvironmental regulation of oligodendrocyte replacement and remyelination in spinal cord injury", J Physiol 594.13 (Jul. 1, 2016) pp. 3539-3552.
Linares et al., "Neuronal nitric oxide synthase plays a key role in CNS demyelination", J Neurosci . Dec. 6, 2006;26(49):12672-81.
Berg et al., "Neuro-oxidative-nitrosative stress in sepsis", Journal of Cerebral Blood Flow and Metabolism. Apr. 13, 2011; 31:1532-1544.
Sonar et al., "The iNOS Activity During an Immune Response Controls the CNS Pathology in Experimental Autoimmune Encephalomyelitis", Front. Immunol. 10:710, Apr. 4, 2019.
Galea et al., "Inhibition of mammalian nitric oxide synthases by agmatine, an endogenous polyamine formed by decarboxylation of arginine", Biochem J. May 1, 996, 15;316 (Pt 1):247-9.

(Continued)

Primary Examiner — Dale R Miller
(74) Attorney, Agent, or Firm — Maschoff Brennan

(57) ABSTRACT

The invention disclosed herein relates to a novel synergistic nutritional composition for promoting axonal regeneration. Particularly, the present invention provides potent nutritional composition comprising synergistic exogenous blend of agmatine (decarboxylated L-arginine) and inosine monophosphate (IMP) and salts thereof, which are present in a weight ratio of 1:0.05 to 1:2 along with pharmaceutically acceptable excipients. The instant synergistic nutritional composition is useful for treating diseases or disorders related to traumatic injury in the central nervous system such as brain or spinal cord injury, optic nerve lesions.

14 Claims, 3 Drawing Sheets

(56) References Cited

OTHER PUBLICATIONS

Auguet et al., "Selective inhibition of inducible nitric oxide synthase by agmatine.", Japan Journal of Pharmacology 69, 1 3, Nov. 1, 1995, 285-287.

Satriano et al., "Suppression of inducible nitric oxide generation by agmatine aldehyde: beneficial effects in sepsis", J Cell Physiol. Sep. 2001;188(3):313-20.

Halaris et al., "Agmatine: metabolic pathway and spectrum of activity in brain", CNS Drugs 21:885-900—Jul. 2007.

Jospeh Satriano, "Agmatine: at the crossroads of the arginine pathways", Ann N Y Acad Sci. Dec. 2003; 1009:34-43.

Anderson et al., "Upregulation of complement inhibitors in association with vulnerable cells following contusion-induced spinal cord injury." J Neurotrauma. Mar. 2005; 22:382-397.

Cudrici et al., "C5b-9 Terminal Complex Protects Oligodendrocytes from Apoptotic Cell Death by Inhibiting Caspase-8 Processing and Up-Regulating FLIP", J Immunol Mar. 1, 2006; 176:3173-3180.

Rus et al., "The complement system in central nervous system diseases", Autoimmunity, Aug. 2006; 39(5): 395-402.

Devine DV, "The regulation of complement on cell surfaces", Transfusion Med Rev Apr. 5, 1991; 5: 123-131.

B P Morgan, "Regulation of the complement membrane attack pathway", Crit Rev Immunol. Jan. 1, 1999;19(3):173-98.

Xiong et al., "Formation of Complement Membrane Attack Complex in Mammalian Cerebral Cortex Evokes Seizures and Neurodegeneration" Journal of Neuroscience Feb. 1, 2003, 23 (3) 955-960.

Lorber et al., "Mst3b, an Ste20-like kinase, regulates axon regeneration in mature CNS and PNS pathways" Nat Neurosci. Nov. 2009;12(11):1407-14.

* cited by examiner

SYNERGISTIC NUTRITIONAL COMPOSITIONS FOR PROMOTING AXONAL REGENERATION

FIELD OF THE INVENTION

The present invention relates to novel synergistic nutritional compositions for promoting axonal regeneration. Particularly, the present invention provides potent nutritional composition comprising synergistic exogenous blend of agmatine (AGM) (decarboxylated L-arginine) and inosine monophosphate (IMP) and salts thereof, present in suitable weight ratio, along with pharmaceutically acceptable excipients.

The present synergistic nutritional composition is useful for treating diseases or disorders related to traumatic injury in the central nervous system such as brain or spinal cord injury, or optic nerve lesions.

BACKGROUND OF THE INVENTION

The central nervous system (CNS) controls most functions of the body and mind. It consists of two parts: the brain and the spinal cord. The spinal cord is the highway for communication between the body and the brain. When the spinal cord is injured, the exchange of information between the brain and other parts of the body is disrupted. Many organs and tissues in the body can recover after injury without intervention. However, some cells of the central nervous system are so specialized that they cannot generate new cells. As a result, recovery from a brain or spinal cord injury is much more difficult.

The complexity of the central nervous system makes the formation of the required connections between brain and spinal cord cells, very difficult. It is a huge challenge for scientists to recreate the central nervous system that existed before the injury. According to the World Health Organization (WHO) report, every year around the world, between 250,000 to 500,000 people suffer from a spinal cord injury (SCI).

As reported by the National Spinal Cord Injury Association, approximately 450,000 people in the United States are living with a spinal cord injury (SCI). Other organizations conservatively estimate this figure to be about 250,000. Every year, an estimated 17,000 new SCIs occur in the U.S. Most of these are caused by trauma to the vertebral column, thereby affecting the spinal cord's ability to send and receive messages from the brain to the body's systems that control sensory, motor, and autonomic function below the level of injury. There is no reliable estimate of global prevalence, but estimated annual global incidence is 40 to 80 cases per million population. Up to 90% of these cases are due to traumatic causes, though the proportion of non-traumatic spinal cord injury appears to be growing. Mortality risk is highest in the first year after injury and remains high compared to the general population. People with spinal cord injury are two to five times more likely to die prematurely than people without spinal cord injury, with worse survival rates in low- and middle-income countries.

Generally, corticosteroid drugs like methylprednisolone or glucose-lowering agents like metformin are prescribed in the treatment of SCI, however, steroid medication can weaken the immune system, making it easier to get an infection, or worsening an infection and under certain conditions metformin can cause lactic acidosis. Therefore, it is required to find out remedy for treating SCI or axonal damage that can be derived from natural sources to alleviate the side effects associated with existing drugs. The term 'spinal cord injury' (SCI) refers to damage to the spinal cord resulting from trauma or from disease or degeneration.

Further, it is observed that dysfunction and death of retinal ganglion cells (RGCs) due to traumatic optic nerve injury is a leading cause of visual impairment. Axon regeneration is critical for functional recovery of vision following optic nerve injury. After optic nerve injury, RGC axons usually fail to regrow and die, leading to the death of the RGCs and subsequently inducing the functional loss of vision. However, the detailed molecular mechanisms underlying axon regeneration after optic nerve injury remain poorly understood. Till date, neither pharmacological nor surgical interventions are sufficient to halt or reverse the progress of visual loss [*Curr Neuropharmacol.* 2017 August; 15(6): 861-873].

Axonal regeneration is a fundamental step in the process of recovering from spinal cord injury (SCI). However, the axons in the adult central nervous system (CNS) cannot regenerate easily, which primarily causes lack of adequate restorative therapy for the SCI. Therefore, the need arises to fix the underlying cause of spinal cord or optic nerve injury which is nothing but related to axon and neuronal degeneration.

Neurons (also called nerve cells) are the fundamental units of the brain and nervous system. Neurons connect with one another to send and receive messages in the brain and spinal cord. There are approximately 100 billion neurons in the brain and spinal cord combined. Each neuron is made up of a cell body, which houses the nucleus. Axons and dendrites form extensions from the cell body. Motor neurons of the spinal cord are part of the central nervous system (CNS) and connect to muscles, glands and organs throughout the body. These neurons transmit impulses from the spinal cord to skeletal and smooth muscles, and so directly control all of our muscle movements.

Astrocytes, a kind of glial cell, are the primary support cells of the brain and spinal cord. They make and secrete proteins called neurotrophic factors. They also break down and remove proteins or chemicals that might be harmful to neurons (for example, glutamate, a neurotransmitter that in excess amount causes cells to become overexcited and die by a process called excitotoxicity). Astrocytes are not always beneficial, after injury, they divide to make new cells that surround the injury site, forming a glial scar that is a barrier to regenerating axons.

Microglia is immune cells for the brain. After injury, they migrate to the site of injury to help clear away dead and dying cells. They can also produce small molecules called cytokines that trigger cells of the immune system to respond to the injury site. This clean-up process is likely to play an important role in recovery function following a spinal injury. Oligodendrocytes are glial cells that produce a fatty substance called myelin which wraps around axons in layers. Axon fibers insulated by myelin can carry electrical messages (also called action potentials) at a speed of 100 meters per second, while fibers without myelin can only carry messages at a speed of one meter per second. In the central nervous system (CNS), oligodendrocytes are responsible for myelination by wrapping around the axon and maintaining saltatory conduction. Damage to oligodendrocytes and the myelin sheath around nerves is termed demyelination. Demyelination of axons causes the multitude of neurological symptoms found in different diseases like multiple sclerosis and SCI. Dysmyelination is the abnormal formation of the myelin sheath. This is implicated in several leukodystrophies, and also in schizophrenia [*Pediatr Radiol* 21, 477-482 (1991)].

Central nervous system (CNS) axons do not spontaneously regenerate after injury in adult mammals. In contrast, peripheral nervous system (PNS) axons readily regenerate, allowing recovery function after peripheral nerve damage. It is suggested that the PNS environment is stimulatory and/or that the CNS environment is inhibitory for axon growth. Subsequent studies have identified both growth-promoting factors in the PNS and growth-inhibiting factors in the CNS. Inhibitors of regeneration include specific proteins in CNS myelin and molecules associated with the astroglia scar. In addition, slower debris clearance in the CNS relative to the PNS may impede axonal re-growth. The cell-autonomous failure of the cell of axotomized CNS neurons to induce those growth-promoting genes, which are highly upregulated by injured PNS neurons also limits brain and spinal cord repair. An understanding of factors which influence axon growth is critical for the development of therapeutics to promote CNS regeneration.

Cell-autonomous factors are also important determinants of CNS regeneration failure. CNS neurons do not upregulate growth-associated genes to the same extent as PNS neurons. Consequently, their ability to regenerate is limited even in the absence of inhibitors. Increasing the intrinsic growth capacity of neurons allows modest axon regeneration within the CNS [*Results Probl Cell Differ.* 2009; 48: 339-351].

Axon regeneration is one of the many factors influencing recovery after CNS damage. Sprouting of uninjured axons can also contribute dramatically to functional improvements. Additionally, plasticity at the synaptic level may underlie a certain degree of recovery seen even in the absence of treatments. Axon degeneration is a characteristic event that occurs in many neurodegenerative conditions including glaucoma, stroke, traumatic brain injury, and motor neuropathies. Particularly axonal degeneration occurs in at least three phases—an acute and rapid degeneration phase on both sides of the lesion, followed by a period of quiescence/latency, then rapid cytoskeletal disassembly, fragmentation and granular degeneration of the axon distal to the injury site [Coleman and Freeman, *Annu. Rev. Neurosci.* 2010. 33:245-67].

When an axon is crushed, an active process of axonal degeneration takes place at the part of the axon furthest from the cell body. This degeneration takes place quickly following the injury, with the part of the axon being sealed off at the membranes and broken down by macrophages. This is known as Wallerian degeneration.

Spinal cord injury (SCI) remains a major challenge to neurological research. Progress in both basic and clinical research has shown that neurons and oligodendrocytes are equally susceptible to such injury. In injuries secondary to direct injury to the spinal cord, oligodendrocytes appear to be highly vulnerable to various harmful factors and eventually undergo apoptosis. Due to the loss of myelinating cells, axonal demyelination is likely to affect the neural function of surviving axons. Recently, improved understanding of the pathological changes ongoing in oligodendrocytes following injury has shown that the death of these cells plays a vital role in the demyelination of axons. Because the demise of oligodendrocytes and subsequent axonal demyelination impairs the conductive capacity of surviving axons, it seems reasonable to expect that reducing oligodendrocyte death and improving axonal myelination holds potential for the treatment of SCI [*J Neurotrauma.* 2009 October; 26(10): 1847-56].

Cells from the immune system migrate to the injury site, causing additional damage to some neurons and death to others that survived the initial trauma. Recent research has shown that there are at least three different mechanisms of cell death at play in neuronal and oligodendrocyte loss after injury: necrosis, excitotoxicity, and apoptosis. The spinal cord injury is mainly caused by pressing a spinal cord through a displacement of spine due to a traumatic injury. A necrosis is caused immediately after damage along with a mechanical primary damage, apoptosis of oligodendrocyte in the white matter and a neuronal cell of a grey matter is caused due to a slowly generated apoptosis, and a demyelination of axon is caused, thereby ultimately generating a permanent functional disorder.

Considering pathophysiologic analysis, it is observed that secondary spinal cord injury involves the apoptotic as well as necrotic death of neurons and glial cells. Further the major factors that can contribute to cell death, such as glutamatergic excitotoxicity, free radical damage, cytokines, ATP depletion; an ischemia due to a hypoxia environment and inflammation due to inflammatory mediators, such as iNOS, or proinflammatory cytokines, such as TNF-α, IL-1β [*Spine* (Phila Pa 1976). 2000 Jul. 15; 25(14):1859-66]. Among these factors, the inflammatory reaction lasts through a long period as well as at the very beginning. Especially, apoptosis that slowly progresses or an inflammatory reaction due to microglia in axon degeneration is pathologic property that is commonly exhibited in most nerve diseases as well as a spinal cord injury [*TRENDS in Molecular Medicine Vol.* 10 No. 12; 2004].

Consequently, the death of oligodendrocytes causes axons to lose their myelination, which greatly impairs the conduction of action potential, messages, or renders the remaining connections useless. The neuronal information highway is further disrupted because many axons are severed, cutting off the lines of communication between the brain and muscles and between the body's sensory systems and the brain. In the central nervous system (CNS), oligodendrocytes are specialized glial cells responsible for myelin formation and maintenance. Following spinal cord injury (SCI), oligodendroglia cell death and myelin damage (demyelination) cause chronic axonal damage and irreparable loss of sensory and motor functions. Accumulating evidence shows that replacement of damaged oligodendrocytes and renewal of myelin (remyelination) are promising approaches to prevent axonal degeneration and restore function following SCI.

Axon demyelination (loss of myelin sheath) occurs following oligodendrocyte death caused by trauma, autoimmune disorders, infections, genetic defects, or idiopathic reasons. Demyelination disrupts the precise organization of ion channels in the axolemma causing ionic imbalance and high energy consumption for signal conduction. Increased energy demand together with loss of trophic support from oligodendrocytes, can increase the susceptibility of demyelinated axons to loss of energy homeostasis, oxidative stress, and degeneration. Therefore, oligodendrocyte replacement and axon remyelination are vital repair mechanisms for restoring function following SCI.

Importantly, accelerating remyelination can maintain the integrity of surviving axons and attenuate chronic axonal loss following injury. Identification of key extrinsic factors involved in myelin damage and repair is a vital step in the development of effective therapeutic strategies for promoting remyelination after CNS injury or disease [*J Physiol* 594.13 (2016) pp 3539-3552].

Nitric oxide (NO) is a small, short-lived molecule released from a variety of cells that is implicated in a multitude of biological processes. In pathological conditions, overproduction of NO may lead to the generation of highly reactive species, such as peroxynitrite and stable nitrosothiols that may cause irreversible cell damage. It is evident that increased concentrations of NO in the CNS are usually attributed to an increase in the inducible isoform of NO synthase (iNOS) usually produced by inflammatory cells. [*J Neurosci.* 2006 Dec. 6; 26(49):12672-81]. Furthermore, the NO produced by iNOS in glia cells or by nNOS under excitotoxic process can form with free radicals (particularly $O^{2-}$) O N O O$^-$ and produce several deleterious effects on tissue. These free radicals can further decompose into highly toxic-free radicals, such as $NO_2$. and .OH [*Journal of Cerebral Blood Flow and Metabolism.* 2011; 31:1532-1544].

Under physiological conditions, the concentration of NO fluctuates within the range of low values and is produced mainly by nNOS and eNOS. Unlike the other two enzymes, iNOS is not expressed unless it is induced by inflammatory mediators, cytokines, and other agents, such as endotoxins. Due to its calcium-independent activation, iNOS can produce a large amount (100-1000 times greater) of NO in relation to eNOS and nNOS. Until the enzyme is degraded, iNOS constitutively produces NO.

Cytokines are cell signalling molecules that aid cell to cell communication in immune responses and stimulate the movement of cells towards sites of inflammation, infection, and trauma. Further cytokines induce the expression of iNOS in macrophages and microglial cells which leads to the generation of higher NO and peroxynitrite productions, and cause tissue destruction in the CNS [*Front. Immunol.* 10:710, 2019] Several studies have shown that iNOS can regulate the function of regulatory dendritic cells (regulatory DCs) which in turn can induce apoptosis of inflammatory cells and help in controlling the inflammation of the brain and spinal cord. Furthermore, iNOS expression in macrophages is linked with the suppression of inflammasome activation-induced IL-1β production as well as a reduction in the frequency of M1 macrophages. During chronic demyelination, a pathogenic phenotype of microglial cells has been found to be associated with iNOS expression. Some in vitro experiments suggest that inflammatory cytokine-induced iNOS reduces the expression of myelin proteins and causes oligodendrocyte death in the mixed glial cultures. All these observations indicate that iNOS plays a dual role during neuronal autoimmunity [*Front. Immunol.* 10:710, 2019].

A study published in 1997 found that when a spinal cord injury is generated, an excitotoxicity neurotransmitter, a free radical, inflammatory mediator, and the like are generated so that apoptosis is induced. Concisely, the high levels of iNOS produced in the CNS might have caused apoptosis of oligodendrocytes in the brain, and thus contributed to increase the clinical severity of the inflammation of the brain and spinal cord. Therefore, it is needful to inhibit the expression of inducible nitric oxide synthase (iNOS) enzyme. Particularly it is required to find out potential bioactive ingredients that can suppress or inhibit necrotic and apoptotic cell death of oligodendrocytes, precisely there is a need for a therapeutic agent that selectively hampers iNOS enzyme expression.

The inventors of the present application found that the decarboxylate derivative of L-arginine called agmatine is a competitive inhibitor of iNOS [NOS2 or NOS II]. E. Galea et al. [*Biochem J.* 1996, 15; 316 (Pt 1):247-9] discloses Agmatine, as an endogenous regulator of NO production in mammals. Agmatine competitively inhibits NOSs, most potently the inducible isoform. Agmatine is potent as aminoguanidine to inhibit the activity of the inducible form of nitric oxide synthase (iNOS) and devoid of significant activity on the constitutive form of NOS [*Japan Journal of Pharmacology* 69, 13, 1995, 285-287].

Further, WO98/13037 A1 provides methods of selectively inhibiting inducible nitric oxide synthase (iNOS), while maintaining constitutive nitric oxide synthase (cNOS), by administering an arginine derivative i.e, agmatine-aldehyde (guanidinobutyraldehyde). Further Satriano J, et al. has disclosed that agmatine aldehyde control inflammation by suppressing iNOS mediated NO generation [*J Cell Physiol.* 2001 September; 188(3):313-20]. Additionally, agmatine irreversibly inhibits neuronal nitric oxide synthase (nNOS) and down-regulates inducible nitric oxide synthase (iNOS). Brain inductions of agmatine seem to occur in astrocytes, although neurons also synthesize agmatine [*CNS Drugs* 21:885-900•July 2007].

Agmatine is an antiproliferative molecule due to its suppressive effects on intracellular polyamine levels, whereas the aldehyde metabolite of agmatine is a potent inhibitor of iNOS. [*Ann N Y Acad Sci.* 2003 December; 1009:34-43]. Surprisingly, the inventors of the present application observed that inflammation and complement activation are tractable targets in neuroinjury and neurodegenerative disease. The complement system plays critical roles in development, homeostasis, and regeneration in the central nervous system (CNS) throughout life; however, complement dysregulation in the CNS can lead to damage and disease. The soluble complement regulators are elevated in lesioned neurons and oligodendrocytes with the deposition of complement proteins at sites of SCI.

Recent studies by [Anderson et al *J Neurotrauma.* 2005; 22:382-397] demonstrated that complement proteins are deposited at sites of SCI on neurons and oligodendrocytes for a sustained period following injury in rats. In a subsequent study, it has been shown that the complement inhibitory proteins factor H and clusterin are present at increased levels among neurons and oligodendrocytes after SCI in rats, and it was suggested that these complement inhibitors function to limit the inflammatory reaction in the injured spinal cord.

Particularly complement activation with assembly of the terminal complement complex C5b-9, consisting of the C5b, C6, C7, C8, and C9 proteins, plays a significant role in the pathogenesis of a variety of CNS diseases. By forming pores in the plasma membrane, C5b-9 can cause cell death and also induce apoptosis. However, OLG, like other nucleated cells, can survive limited C5b-9 complement attack through the protection provided by complement-inhibitory proteins and by elimination of membranes carrying C5b-9 complexes [*J Immunol* 2006; 176:3173-3180].

Activation of the complement system is important factor in the pathogenesis of inflammatory, neurodegenerative and cerebrovascular diseases. OLG, myelin and neurons are susceptible to complement-mediated cell damage. Administration of complement inhibitors has been shown reduction in the severity of the diseases like encephalomyelitis, cerebral ischemia, stroke, and neurodegenerative disorders that suggest an important pathogenetic role for complement. It is important to note that OLG can survive limited complement attack by shedding cell membranes enriched with C5b-9 complexes [*Autoimmunity*, August 2006; 39(5): 395-402]. Complement consists of a complex collection of approximately plasma-soluble proteins, many of which are zymogens. Activation of complement can occur along two possible pathways, the classical and alternative pathways both of which result in the formation of the membrane attack complex (MAC) [*Transfusion Med Rev* 1991; 5: 123-131].

The MAC inserts into cell membranes to form a functional pore, resulting in ion flux and ultimately osmotic lysis. Complement is an important member of the innate immune system. Although diverse mechanisms can activate complement, each activation pathway culminates in the formation of C5b, the first component of the membrane attack pathway. Once formed, C5b binds to C6 to produce a stable and soluble complex, C5b6. Next, C7 binds C5b6 to form C5b7, which can attach to the surface of cell membranes without disturbing membrane integrity. The binding of C8 to the membrane bound C5b7 forms C5b8, which becomes more deeply incorporated in the membrane and causes the cell to become slightly leaky. The C5b8 complex in turn forms a receptor for C9 molecules. The binding of the initial C9 molecule to C5b8 transforms the C9 molecule from a globular, hydrophilic structure to an elongated, amphipathic structure, which inserts into and through the membrane; these conformational changes in C9 expose binding sites for additional C9 to bind, unfold, and insert into the membrane. Addition of as many as 18 copies of C9 to the C5b8 complex forms the membrane attack complex (MAC), resulting in ion flux and ultimately lysis of target cells [*Crit Rev Immunol.* 1999; 19(3):173-98] [*Journal of Neuroscience* 2003, 23 (3) 955-960]. The formation of MAC contributes directly to neuronal injury and demyelination.

Hence, there is an ongoing need for therapeutic compositions comprising bioactive compounds that can be used in the prophylaxis and/or treatment of disorders mediated by an undesired activity of the complement system, which includes MAC deposition or assembly.

There are some compositions known in the art which describe MAC inhibitors or complement system. WO2014096958A1 relates to inosine monophosphate (IMP) and functional equivalent thereof for to counteract the formation of the (MAC) which is useful in the treatment of acute and chronic nerve injuries, preferably to promote axonal regeneration after such injuries have occurred. EP1624894A4 discloses inosine-containing compound for increasing functionality of the dendritic cells. Further EP1009412B1 describes use of inosine for stimulating the axonal outgrowth of central nervous system neurons following a stroke episode.

The inventors of the present invention have further analyzed that mammalian sterile 20-like kinase-3b (Mst3b) plays essential role in axonal regeneration. It is observed that mammalian sterile 20-like kinase-3b (Mst3b, encoded by Stk24), regulates axon outgrowth or mediates the axon-promoting effects of trophic factors in retinal ganglion cells (RGCs) and dorsal root ganglion (DRG) neurons, and is essential for axon regeneration in vivo. Conversely, expression of constitutively active Mst3b enabled both types of neurons to extend axons without growth factors. In vivo, RGCs lacking Mst3b failed to regenerate injured axons when stimulated by intraocular inflammation. DRG neurons regenerating axons in vivo showed elevated Mst3b activity and reducing Mst3b expression attenuated regeneration and p42/44 MAPK activation. Thus, Mst3b regulates axon regeneration in both CNS and PNS neurons. [*Nat Neurosci.* 2009 November; 12(11):1407-14].

Further U.S. Pat. No. 8,912,144B2 discloses inosine induces several types of neurons to extend axons in culture, including those of the embryonic cortex. Inosine diffuses across the cell membrane and activates Mst3b, a Ste20-like protein kinase that plays a central role in the signal transduction pathway through which trophic factors induce axon outgrowth. Increasing Mst3b expression promotes axonal regeneration of spinal cord neurons, which led to behavioral and electrophysiological improvement. On the contrary downregulation of Mst3b level have the adverse effects.

In view of existing prior art and research in the field of neurons, the inventors have observed that imbalanced levels of factors that promote cell death among newly generated oligodendrocytes and activation of complement system are considerably major factors for inhibiting axonal sprouting and/or regeneration. Consequently, the need arises to survive the oligodendrocytes or promote oligodendrogenesis, myelinogenesis during or after SCI.

Moreover, the renewal of myelin sheath around surviving demyelinated axons following injury in combination with complement inhibition is found to be vital repair strategy for CNS regeneration and functional recovery. Therefore, the present inventors have developed innovative therapeutic intervention by introducing exogenous blend of naturally derived amino acid along with nucleoside monophosphate that shows synergistic and significant results in axonal regeneration without any side effects.

OBJECTIVES OF THE INVENTION

The primary objective of the present invention is to provide promising therapeutic approach, for promoting axonal regeneration.

Another objective of the invention is to provide cost-effective, side-effect-free nutritional composition for treating traumatic injury in the central nervous system.

Yet another objective of the invention is to provide nutrient based medicinal approach for reducing myelin-forming oligodendrocytes apoptosis and inhibiting complement protein expression/deposition.

Additional objective of the invention is to provide nutritional composition that ameliorates metal-binding capacity and plasticity of metallothioneine.

Further objective of the invention is to provide combination of biologically active, safe, nontoxic, naturally derived nutrients for promoting axonal growth, sprouting, regeneration, and functional plasticity after spinal cord injury.

Another objective of the invention is to provide administration of nutritional composition in patients with spinal cord injury that leads to nerve repairing or stimulating the regeneration after spinal cord injury without any adverse effects.

SUMMARY OF THE INVENTION

To meet the above objectives, the inventors of the present invention carried out thorough experiments to establish significant effect of the bioactive ingredients or amino acid derivatives or nucleoside monophosphate or food ingredients or nutrients or generally recognized as safe active ingredients present in the composition that ameliorate axon regeneration and neurological recovery after spinal cord injury.

In particular aspect, the invention relates to synergistic nutritional compositions comprising therapeutically active nutrients along with pharmaceutically acceptable carriers for regulating myelination and axonal growth or regulating myelin and axon biology or regulating neural circuit function.

In another particular aspect, the invention provides novel synergistic nutritional compositions comprising synergistic combination of decarboxylated amino acid derivative and nucleoside monophosphate present in suitable weight ratio, along with pharmaceutically acceptable excipients, wherein decarboxylated amino acid derivative is agmatine salt; and nucleoside monophosphate is inosine monophosphate salt.

In another aspect, the present invention provides naturally occurring nutrient based synergistic compositions for promoting axonal remyelination and simultaneously preventing demyelination and activation of complement and the subsequent formation of C5b-9 channels or (MAC).

In a further aspect, the present invention provides biologically active complex exhibiting neuroregenerative and neuroprotective activity comprising synergistic combination of AGM and IMP and salts thereof which are present in specific weight ratio, along with pharmaceutically acceptable carriers.

In a further aspect, the present invention provides novel and potent nutritional composition; wherein the administration of said composition synergistically enhances neuronal survival, promotes axon growth and axon regeneration by regulating factors that negatively affecting CNS environment.

In the present invention, the agmatine (AGM) treatment boosts the regeneration of damaged oligodendrocytes, prevents myelin loss, and assists in enhancing axonal remyelination by suppressing iNOS mediated NO generation and ameliorates metal-binding capacity and plasticity of metallothioneine.

Simultaneously or concomitantly inosine monophosphate (IMP) treatment prevents breakdown of neuronal tissue or injured nerves by inhibiting formation of membrane attack complex (MAC) formation and complement activation. IMP mediated MAC inhibition prevents demyelination and microglia/macrophage activation. Further Inosine crosses the cell membrane and, in neurons, activates Mst3b, a protein kinase that that regulates axon outgrowth. Further, the administration of inosine raises the serum uric acid (metabolic end product of inosine) levels that impact secondary pathology in nerve injury by directly preventing peroxynitrite-mediated cell toxicity or interfering with the acute inflammatory response.

In another aspect, the invention provides cost effective, non-toxic, efficient, and environmentally safe, exogenous nutritional composition comprising synergistic combination of food grade, generally recognized as safe ingredients for nerve repairing or stimulating neuroregeneration after spinal cord injury without adverse effects.

In yet another aspect, the invention relates to synergistic nutritional compositions comprising combination of AGM salt which is present in the range of 1 to 2000 mg; and IMP salt is present in the range of 1 to 2500 mg along with pharmaceutically acceptable excipients/carriers, optionally in presence of bioenhancer.

In yet one more aspect, the invention provides synergistic nutritional composition which is useful for treating diseases or disorders which are associated injured central nervous system (CNS) axons such as brain or spinal cord injury, optic nerve lesions.

Moreover, the instant synergistic nutritional composition is useful for treating diseases or disorders which are associated with demyelination, myelin sheath degeneration, axonal dysfunction, axonal damage, and axonal degeneration.

Abbreviations

AGM: Agmatine Sulphate
IMP: Inosine monophosphate
MAC: Membrane attack complex
TCC: Terminal complement complex
OLG: oligodendrocytes
C5b-9: Complement component/complement proteins (sub-unit 5b, 6, 7, 8 and 9)
SCI: Spinal cord injury
CNS: central nerve system
PNS: Peripheral nerve system
Mst3b: mammalian sterile 20-like kinase-3b
MTs: Metallothioneins
iNOS: Inducible nitric oxide synthase
NO: Nitric Oxide

DETAILED DESCRIPTION OF THE INVENTION

Figure 1:
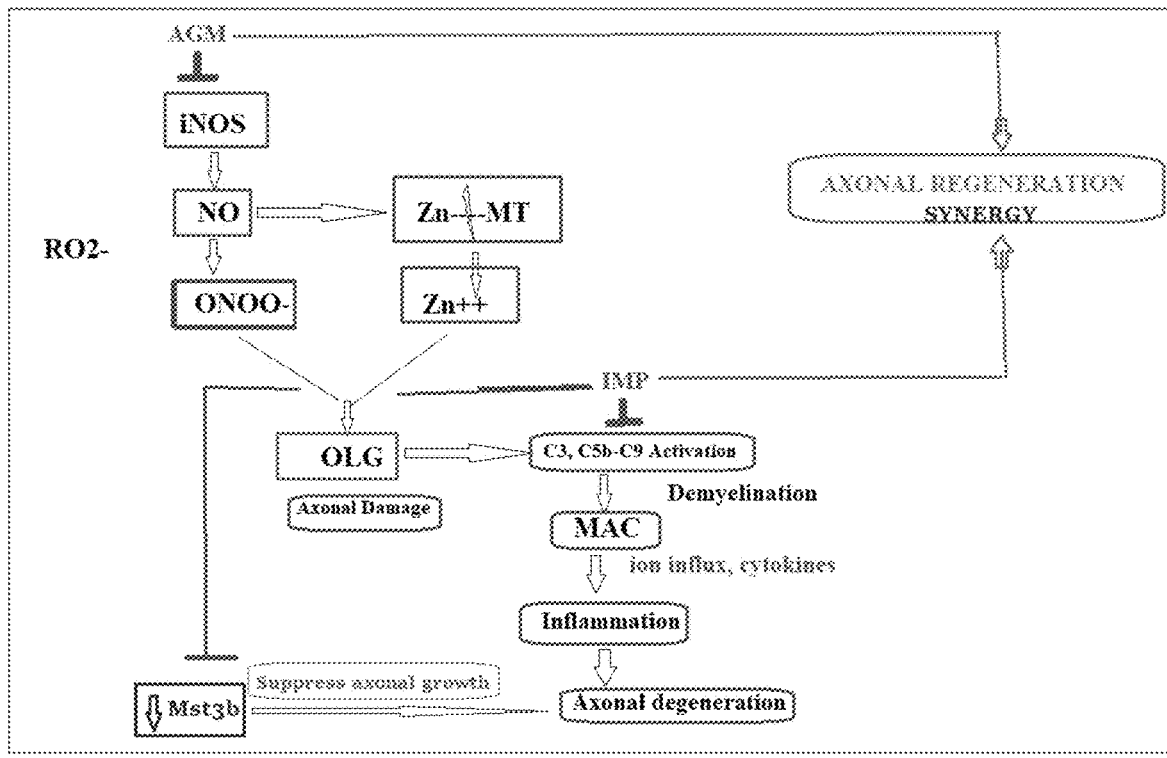
FIG. 1 illustrates schematic representation of synergistic effect of AGM and IMP in axonal regeneration.

The invention will now be described in detail in connection with certain preferred and optional embodiments, so that various aspects thereof may be more fully interpreted and comprehended.

However, any skilled person or artisan will appreciate the extent to which such embodiments could be generalized in practice. It is further to be understood that all terminology used herein is for the purpose of describing particular embodiments only and is not intended to be limiting in any manner or scope.

Unless defined otherwise, all technical and scientific expressions used herein have the same meaning as commonly understood by one of ordinary skill in the art to which embodiments of the invention pertain. In describing and claiming the embodiments of the present invention, the following terminology will be used in accordance with the definitions set out below which are known in the state of art.

The singular forms "a," "an," and "the" include plural reference unless the context clearly dictates otherwise. Also, the term 'composition' does not limit the scope of the invention for multiple compositions that can be illustrated for best mode of the invention.

The term "pharmaceutically/nutraceutically acceptable salt," as use herein, represents those salts which are within the scope of sound medical judgment, suitable for use in contact with the tissues of humans and animals without undue toxicity, irritation, allergic response, and the like and are commensurate with a reasonable benefit/risk ratio. Particularly the term "pharmaceutically-acceptable salts" refers to the relatively non-toxic, inorganic, and organic acid addition salts of compounds, alkali or alkaline earth metal salts, as well as solvates, co-crystals, polymorphs and the like of the salts.

All modifications and substitutions that come within the meaning of the description and the range of their legal equivalents are to be embraced within their scope. A description using the transition "comprising" allows the inclusion of other elements to be within the scope of the invention.

In one embodiment, the invention provides novel, potent synergistic nutritional composition for promoting axonal regeneration, comprising combination of decarboxylated amino acid derivative and nucleoside monophosphate.

In a preferred embodiment, the invention provides potent synergistic nutritional composition for promoting axonal regeneration, comprising combination of agmatine sulphate and inosine monophosphate disodium salt hydrate present in suitable weight ratio, along with pharmaceutically acceptable excipients.

In another preferred embodiment, the invention provides potent synergistic nutritional composition for nerve repairing or stimulating neuroregeneration after spinal cord injury, wherein the one active moiety is decarboxylated amino acid.

According to the invention the amino acid is L-arginine and its decarboxylated form is 'Agmatine'. Agmatine is chemically known as 4-(aminobutyl) guanidine represented below as Formula I. The agmatine salt is preferably agmatine sulphate.

Formula I

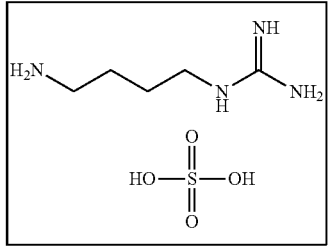

Agmatine is a natural metabolite of the amino acid arginine. It is formed when arginine is decarboxylated by the enzyme arginine decarboxylase.

Agmatine modulates the balance between other L-arginine metabolic pathways via its influence on the production of nitric oxide (NO). Production of nitric oxide through iNOS is associated with higher and more persistently elevated levels of NO. When NO is produced in an environment of oxidative stress, such as following SCI, NO combines with the superoxide radical to form the highly reactive oxidizing agent, peroxynitrite.

In another embodiment, the invention provides agmatine as potent iNOS inhibitor, wherein it controls NO induced axonal damage, particularly oligodendrocytes damage.

In another embodiment, the invention provides synergistic nutritional composition wherein the effective amount of AGM salt suppresses NO induced necrosis and apoptosis of oligodendrocytes which is observed in the chronic phase of injury.

Oligodendrocytes produce myelin sheaths in the CNS. The myelin sheaths are essential for saltatory signal conduction and tropic support to maintain axonal integrity. Unfortunately, mature oligodendrocytes, the only myelin-forming cells within the CNS, are highly susceptible to damage. An acute loss of oligodendrocytes, along with neuronal death, occurs faster after SCI that leads to aggravated demyelination.

Besides the initial acute insults, both necrosis and apoptosis of oligodendrocytes have been observed in the chronic phase of injury. Numerous factors may contribute to this process including the overabundant release of proinflammatory cytokines, uncontrolled oxidative stress, glutamate- and ATP-mediated excitotoxicity and iNOS induced NO release. Moreover, oligodendrocytes and intact myelin sheath are primarily responsible for the facilitation of neuronal signal conduction. There is potential role of oligodendrocytes in preserving the integrity and survival of axons.

Given the fact that each oligodendrocyte is responsible for 30-80 distinct axons, it could be expected that extensive demyelination may occur even after the collapse of only a single oligodendrocyte. Indeed, axonal integrity relies heavily on oligodendrocyte support and that oligodendrocyte loss would result in axonal degeneration.

The myelin sheaths essentially shield axons from their surroundings and limit access to extracellular metabolites. It maintains metabolic homoeostasis and energy supply to the axons. Furthermore, myelinating oligodendrocytes are able to synthesize and deliver ATP to axons through connexons; this increases the conduction speed of action potentials. On the other side naked or demyelinated axons are more vulnerable to injuries, it is reasonable to expect that, after injury.

In yet another embodiment, the invention provides synergistic nutritional composition with efficient remyelination essential for cellular replacement, neuron-glial cross talk reconstruction and neuronal function recovery through administration of therapeutically effective amount of AGM.

The NO produced by iNOS in glial cells after nerve injury triggers the NMDA-excitotoxic pathway, combines with superoxide anion and results in peroxynitrite synthesis, a potent free radical that contributes to tissue damage in the brain. Further the inducible isoform of nitric oxide synthase (iNOS), produces nitric oxide (NO) from l-arginine in response to inflammatory stimuli. This NO triggers oligodendrocytes necrosis or apoptosis.

In another embodiment, the invention provides synergistic nutritional composition, wherein the agmatine (AGM) treatment boosts the regeneration of damaged oligodendrocytes, prevents myelin loss, and assists in enhancing axonal remyelination by suppressing iNOS mediated NO generation.

Additionally, the agmatine promotes demyelization or phagocytosis of myelin debris and apoptotic cells by targeting or modulating microglial/macrophage function. Metallothioneins (MTs) are a family of small, highly conserved, cysteine-rich metal-binding proteins that are important for divalent metal homeostasis, protection against oxidative stress, and buffering against toxic heavy metals. MTs have the capacity to bind both physiological heavy metals such as zinc, copper, selenium, nickel, and xenobiotic heavy metals such as cadmium, mercury, silver, arsenic through the thiol group of its cysteine residues.

According to the invention metallothionein is a key component of metals like Zn, Cu, Ni signaling system in cells. It is cysteine-rich, metal-binding proteins, acting as scavengers of toxic metal ions or reactive oxygen species. It is observed that iNOS-derived NO nitrosate metallothionein and thereby induce metals like zinc, copper, cadmium, or nickel release. This MT-NO interaction alters in metal homeostasis that leads to neuronal loss or increased susceptibility to oxidative stress and metal-induced neurotoxicity in the brain.

Notably, under pathological conditions, neurotoxic levels of free zinc can accumulate in neurons. The source for this excess zinc not only includes zinc released from synaptic vesicles, but also from other intracellular pools of zinc that can be liberated to form free zinc. When excess zinc floods the synaptic cleft, it enters post-synaptic neurons via glutamate receptors (NMDA and AMPA/kainate) and voltage-gated calcium channels. This excess zinc causes excitotoxicity, induces oxidative stress, and impairs the generation of cellular energy. There is convincing evidence for all three exclusive actions of zinc, acting synergistically to cause neuronal damage and death.

In one embodiment, the invention provides synergistic nutritional composition comprising agmatine as active ingredient which inhibits iNOS-mediated toxic metal release. Moreover, agmatine supports MTs-metal binding affinity.

In another embodiment, the invention provides synergistic nutritional composition, wherein the agmatine improves Zn-binding capacity and plasticity of metallothioneine and thereby reduces $ZN^{2+}$ induced neurotoxicity.

In yet another embodiment, the invention provides synergistic nutritional composition comprising therapeutically effective amount of AGM salt. The dose to be administered usually ranges from 1 mg to 2000 mg, preferably 10 mg to 1500 mg per day.

In another preferred embodiment, the invention provides potent synergistic nutritional composition for nerve repairing or stimulating neuroregeneration after spinal cord injury, wherein the other active moiety is nucleoside monophosphate.

According to the invention, the nucleoside monophosphate is inosine 5' monophosphate salt, more preferably inosine 5' monophosphate disodium salt hydrate represented below as Formula II.

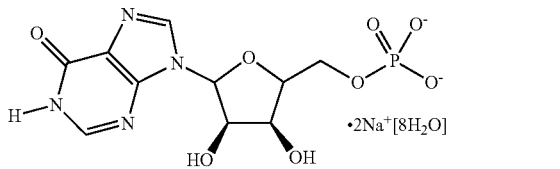

Formula II

Inosinic acid or inosine monophosphate (IMP) or inosine 5'-monophosphate or ribosylhypoxanthine monophosphate is a purine nucleotide which has hypoxanthine as the base and one phosphate group esterified to the sugar moiety. It is chemically known as [(2R,3S,4R,5R)-3,4-dihydroxy-5-(6-oxo-1H-purin-9-yl)oxolan-2-yl] methyl phosphate.

In another embodiment, the invention provides a synergistic nutritional composition wherein the IMP moiety targets the complement system and significantly inhibits or antagonizes MAC formation. The complement inhibitory effect of IMP on MAC formation is particularly noted in nerve crush injury, i.e., disorders that involve complement activation and MAC deposition and activation like SCI. The complement system is a major component of the innate immune system, and a key participant in normal central nervous system (CNS) function. Particularly complement system is involved in neural development, synapse elimination and maturation of neural networks, as well as the progression of pathology in a range of chronic neurodegenerative disorders, and neurotraumatic events such as brain or spinal cord injury, where rapid disruption of neuronal homeostasis potently triggers complement activation.

In another embodiment, the invention provides synergistic nutritional composition, wherein IMP inhibits activation of complement system, moreover it eliminates membrane deposition of C5b-9 proteins/complexes.

According to the invention C5b-9 deposition is found to be associated with cell debris or localized to the plasma membranes of cells adjacent to areas of necrosis. C5b-9 complexes directly participate in the pathogenesis of chronic inflammation and apoptosis. Further MAC insertion triggers Ca2+ influx and increased cytosolic Ca2+ concentration. This increase in intracellular Ca2+ concentration leads to mitochondrial dysfunction, apoptosis, inflammasome activation and IL-1β secretion.

In further embodiment, the administration of effective amount of inosine blocks ion influx after nerve injury, moreover it controls intracellular calcium concentration thereby reduces mitochondrial dysfunction, apoptosis, inflammasome activation and IL-1β secretion.

In one embodiment, the effective amount of inosine blocks MAC formation by inhibiting terminal pathway protein i.e. C6 synthesis, thereby reducing neuronal apoptosis, axonal loss and enhancing neuron performance after injury. Particularly C6 inhibition by inosine controls complement-mediated events in axon loss and subsequent myelin degradation (demyelination) and axonal damage.

In a further embodiment, Inosine, a purine nucleoside stimulates axon outgrowth, through activation of Mst3b kinase activity. Inosine activates Mst3b, an enzyme that is a master regulator of a cell-signaling pathway controlling axon growth. Mst3b, a protein kinase, in turn activates signals that switch on the genes necessary for axons to grow. Peroxynitrite, along with other free radicals, is believed to be involved in the inflammation, demyelination, and axonal injury that occur during injury. Free radical production can increase inflammation and lead to tissue damage. Peroxynitrite is thought to play a role in the demyelination that occurs during nerve injury because of its ability to induce lipid peroxidation of the highly fatty myelin sheath that surrounds the oligodendrocytes (van der Veen et al., *J. Neuroimmunol*, 77, 1-7 1997). Pathological studies have shown that axonal damage in nerve injury is most prevalent in regions with increased inflammation and demyelination, suggesting that axonal damage is also a result of the actions of free radicals and cytokines (Ferguson et al., *Brain.* 1997; 120:393-399).

Peroxynitrite induces strong primary axonal damage with characteristics of primary acute axonopathy, together with severe myelin alteration, myelin vacuolation and demyelination, and nitrotyrosine formation as confirmed by detection of nitrosated target proteins.

In an additional aspect, the protective effect of uric acid (UA) in spinal cord injury is evidently directed at CNS inflammation, because UA treatment prevents the loss of blood-brain barrier (BBB) integrity that occurs in the disease, thereby inhibiting inflammatory cell infiltration. Consequently, raising UA levels may impact secondary pathology in SCI by directly preventing peroxynitrite-mediated cell toxicity or interfering with the acute inflammatory response. Previous studies have shown that uric acid can scavenge hyroxyl radical and peroxynitrite, resulting in reduced oxidative damage to cells.

In the instant invention inosine administration upregulates the serum uric acid levels (metabolic end product of inosine)

that impact secondary pathology in nerve injury by directly preventing peroxynitrite-mediated cell toxicity or interfering with the acute inflammatory response. Remarkably uric acid scavenges hyroxyl radical and peroxynitrite, resulting in reduced oxidative damage to cells.

In yet another embodiment, the invention provides a synergistic nutritional composition comprising therapeutically effective amount of inosine monophosphate disodium salt hydrate. The dose to be administered usually ranges from 1 mg to 2500 mg, preferably 10 mg to 2000 mg per day.

More particularly, the present invention provides stable synergistic effects of combined inosine monophosphate (IMP) with agmatine (AGM) and salts thereof for promoting axonal regeneration. The active moieties of the present composition are present in a therapeutically effective amount. The composition imparts significant effect to the subject in need thereof with enhanced bioavailability and efficacy.

In another embodiment, the invention provides stable, synergistic nutritional compositions for promoting axonal regeneration comprising therapeutically active exogenous combination of inosine monophosphate salt and agmatine salt which are present in specific weight ratio along with pharmaceutically acceptable excipients, wherein inosine monophosphate salt is inosine monophosphate disodium salt hydrate and agmatine salt is agmatine sulphate.

In one preferred embodiment, the invention provides stable, synergistic nutritional compositions for promoting axonal regeneration comprising therapeutically active exogenous combination of crystalline form of inosine monophosphate (IMP) disodium salt hydrate and agmatine sulphate which are present in the weight ratio of 1:0.05 to 1:2 along with pharmaceutically acceptable excipients.

In another preferred embodiment, the invention provides synergistic nutritional compositions for promoting axonal regeneration comprising therapeutically active exogenous combination of white crystalline inosine monophosphate (IMP) disodium salt hydrate and agmatine (AGM) sulphate which are present in the weight ratio of 1:0.1 to 1:1 along with pharmaceutically acceptable excipients.

In one more embodiment, the invention provides synergistic nutritional composition comprising white crystalline inosine monophosphate (IMP) disodium salt hydrate, which is present in a range of 40%-90% by weight of the total composition.

In another embodiment, the invention provides synergistic nutritional composition comprising agmatine (AGM) sulphate, which is present in a range of 10%-55% by weight of the total composition.

In another embodiment the invention provides a synergistic combination of AGM and IMP and salts thereof present in suitable weight ratio along with pharmaceutically acceptable excipients for promoting axonal regeneration, wherein AGM salt not only inhibits iNOS induced NO synthesis but also controls NO induced metal toxicity in neurons; simultaneously IMP salt performs dual role for nerve regeneration; it acts as potent MAC inhibitor as well as activator of Mst3b protein kinase. Inosine also upregulates uric acid expression, which is a natural scavenger for free radicals particularly, uric acid (UA) is a strong peroxynitrite scavenger. This synergistic effect promotes axonal regeneration as well as enhances the fastest recovery of damaged or injured nerves in spinal cord or brain or optic region.

In yet another embodiment, the instant synergistic nutritional composition is useful for treating diseases or disorders which are associated with demyelination, myelin sheath degeneration, axonal dysfunction, axonal damage, and axonal degeneration. The poor regenerative capacity of injured central nervous system (CNS) axons leads to permanent neurological deficits after brain, spinal cord, or optic nerve lesions.

Particularly the disorders are including but not limited to spinal cord injury (SCI), head and spinal cord trauma, hemolytic uremic syndrome, complement mediated kidney disease, ischemia reperfusion disorders, transplant rejection, meningitis, Alzheimer's disease (AD), age-related macular degeneration, multiple sclerosis (MS), Huntington's disease, Parkinson's disease (PD), traumatic brain injury/trauma, Wallerian degeneration (WD), chronic demyelinating neuropathy, atherosclerosis, coronary heart disease, osteoarthritis, Acute Disseminated Encephalomyelitis (ADEM), motor neuron diseases like amyotrophic lateral sclerosis (ALS), Concentric Sclerosis, Charcot-Marie-Tooth Disease (CMT), Guillain-Barre Syndrome (GBS), Neuromyelitis Optica (Devic's Disease), chronic inflammatory demyelinating neuropathies (CIDP), Schilder's Disease, Transverse Myelitis, distal axonopathies, Idiopathic inflammatory demyelinating diseases, metabolic encephalopathies, white-matter diseases (acute haemorrhagic leucoencephalitis, leucodystrophies and central pontine myelinolysis), viral and bacterial infections such as malaria, acquired immunodeficiency syndrome (AIDS) and infection with human lymphotropic virus type 1 (HTLV-I) causing HTLV-I-associated myelopathy (HAM), tropical spastic paraparesis (TSP) and subcortical ischaemic damage, and brain trauma.

In order of degree of severity, injury to a nerve can be described as neurapraxia, axonotmesis, or neurotmesis. Concussion is considered a mild form of diffuse axonal injury. Axonal injury can also cause central chromatolysis. The dysfunction of axons in the nervous system is one of the major causes of many inherited neurological disorders that affect both peripheral and central neurons.

The term "therapeutically effective amount" denotes an amount that reduces the risk, potential, possibility or occurrence of a disease or disorder, or provides advanced alleviation, mitigation, and/or reduction or restoration or modulation, regulation of at least one indicator/biomarker (e.g., blood or serum CRP level), and/or minimize at least one clinical symptom related to SCI.

The term "subject in need thereof" pertains to subject preferably mammal, more preferably human suffering or suspected with nerve injury, particularly with SCI. Particularly, the subject is human with pre-existing or onset symptoms of nerve damage or in a subject to prevent occurrence of nerve injury or subject experience steroid side effects.

In another embodiment the invention provides the potent synergistic nutritional composition, comprising exogenous blend of crystalline inosine monophosphate (IMP) disodium salt hydrate and agmatine sulphate in specific ratio along with pharmaceutically acceptable excipient, wherein the composition activates mst3b-master receptor that controls axon outgrowth.

In another embodiment the invention provides the potent synergistic nutritional composition, comprising exogenous blend of crystalline form of inosine monophosphate (IMP) disodium salt hydrate and agmatine sulphate in the weight ratio of 1:0.05 to 1:2 along with pharmaceutically acceptable excipient, wherein the composition up-regulates plasticity protein Growth Associated Protein 43 [GAP-43], Brain-derived neurotrophic factor [BDNF], nerve growth factor [NGF], Neurotrophin-3 [NTF 3] crucial for axon re-growth, synaptogenesis, innervations and activity of neuro immune cells. Moreover, the present composition significant increase of 3-12 fold in plasticity proteins.

In yet another embodiment the invention provides the potent synergistic nutritional composition, comprising exogenous blend of crystalline form of inosine monophosphate (IMP) disodium salt hydrate and agmatine sulphate in the weight ratio of 1:0.05 to 1:2 along with pharmaceutically acceptable excipient, wherein the present composition achieves more than 98% reduction in CNS ionic zinc concentration.

In yet another embodiment the invention provides the potent synergistic nutritional composition, comprising exogenous blend of crystalline form of inosine monophosphate (IMP) disodium salt hydrate and agmatine sulphate in the weight ratio of 1:0.05 to 1:2 specific ratio along with pharmaceutically acceptable excipient, wherein the present composition achieves more than 98% reduction in CNS ionic zinc concentration.

In yet another embodiment the invention provides the potent synergistic nutritional composition, comprising exogenous blend of crystalline form of inosine monophosphate (IMP) disodium salt hydrate and agmatine sulphate in the weight ratio of 1:0.05 to 1:2, along with pharmaceutically acceptable excipient, wherein the present composition exhibits superior neuron sprouting and re-wiring effects with more than 83% subjects with >1000 axons crossing denervated side.

In some another embodiment the invention provides the potent synergistic nutritional composition, comprising exogenous blend of crystalline form of inosine monophosphate (IMP) disodium salt hydrate and agmatine sulphate in the weight ratio of 1:0.05 to 1:2, along with pharmaceutically acceptable excipient, wherein the present composition achieves highest improvement in limb movement of 0.92 to baseline (as 1).

In the context of the present invention, the term "treatment" relates to alleviate, mitigate, prophylaxis, attenuate, manage, regulate, modulate, control, minimize, lessen, decrease, down regulate, up regulate, moderate, inhibit, restore, suppress, limit, block, decrease, prevent, inhibit, stabilize, ameliorate or cure, heal the nerve degeneration and nerve damage observed in patients with SCI or brain injury.

Notably, the present synergistic composition is non-hazardous, non-toxic, generally recognized safe for human consumption without any adverse effects, therefore the present nutritional composition can also be used under preventive therapy/adjuvant therapy/add-on therapy/combination/adjunctive therapy in a subject in need thereof.

Certain compounds of the present invention can exist in unsolvated forms as well as solvated forms, including hydrated forms. Further some compounds of the present invention can exist in multiple crystalline or amorphous forms ("polymorphs"). In general, all physical forms are of use in the methods contemplated by the present invention and are intended to be within the scope of the invention. Compound or a pharmaceutically acceptable salts, hydrates, polymorphs or solvates of a compound intends the inclusive meaning of "or", in those materials meeting more than one of the stated criteria are included, e.g., a material that is both a salt and a solvate is encompassed.

Compounds of the invention can exist in particular geometric or, enantiomeric or stereoisomeric forms. The invention contemplates all such compounds, including dextrorotatory and levorotatory-isomers, rectus, and sinister configuration. All such isomers, as well as racemic mixtures thereof, are intended to be included in this invention.

In some embodiment, the pharmaceutically acceptable carriers, diluents or excipients are selected from the group consisting of adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or encapsulating agent, such as a liposome, cyclodextrins, encapsulating polymeric delivery systems or polyethylene glycol matrix, which is acceptable for use in the subject, preferably humans. Excipients may also include, for example: antiadherents, antioxidants, binders, coatings, compression aids, disintegrants, dyes (colors), emollients, emulsifiers, fillers (diluents), film formers or coatings, fragrances, glidants (flow enhancers), lubricants, preservatives, sorbents, suspending or dispersing agents, sweeteners, surfactant, anticaking agent, food additives, or waters of hydration.

In some embodiment of the invention, the diluents are selected from starches, hydrolyzed starches, and partially pregelatinized starches, anhydrous lactose, cellulose powder, lactose monohydrate, and sugar alcohols such as sorbitol, xylitol and mannitol, silicified microcrystalline cellulose, ammonium alginate, calcium carbonate, calcium lactate, dibasic calcium phosphate (anhydrous/dibasic dehydrate/tribasic), calcium silicate, calcium sulfate, cellulose acetate, corn starch, pregelatinized starch, dextrin, β-cyclodextrin, dextrates, dextrose, erythritol, ethyl cellulose, fructose, fumaric acid, glyceryl palmitostearate, magnesium carbonate, magnesium oxide, maltodextrin, maltose, medium-chain triglycerides, polydextrose, polymethacrylates, sodium alginate, sodium chloride, sterilizable maize, sucrose, sugar spheres, talc, trehalose, xylitol, vehicles like petrolatum, dimethyl sulfoxide and mineral oil or the like.

In some embodiment of the invention, the amount of diluent in the composition/formulation is present in the range of 1% to 40% by wt. of the total composition/formulation.

In some embodiment, the binder is selected from disaccharides such as sucrose, lactose, polysaccharides and their derivatives like starches, cellulose or modified cellulose such as microcrystalline cellulose and cellulose ethers such as hydroxypropyl cellulose (HPC); hydroxypropyl methyl cellulose (HPMC); sugar alcohols such as xylitol, sorbitol or mannitol; protein like gelatin; synthetic polymers such as polyvinylpyrrolidone (PVP), polyethylene glycol (PEG), starch, acacia, agar, alginic acid, calcium carbonate, calcium lactate, carbomers, carboxymethylcellulose sodium, carrageenan, cellulose acetate phthalate, chitosan, copovidone, corn starch, pregelatinized starch, cottonseed oil, dextrates, dextrin, dextrose, ethyl cellulose, guar gum, hydrogenated vegetable oil, mineral oil, hydroxyethyl cellulose, hydroxymethyl cellulose hydroxyl ethyl methyl cellulose, hydroxypropyl cellulose, inulin, cellulose, methyl cellulose, polyvinylpyrrolidone and polyethylene glycol, lactose, liquid glucose, hypromellose, magnesium aluminum silicate, maltodextrin, maltose, methyl-cellulose, microcrystalline cellulose, pectin, poloxamer, polydextrose, polymethacrylates, povidone, sodium alginate, stearic acid, sucrose, sunflower oil, various animal vegetable oils, and white soft paraffin, paraffin, flavorants, colorants and wax.

In some embodiment of the invention, the amount of binder in the composition/formulation is present in the range of 0.1% to 40% by wt. of the total composition/formulation.

In some embodiment, the antioxidant is selected from tocopherol (vitamin E), sesamol, guaiac resin, mehionine, beta-carotene, lycopene, lutein, zeaxanthin, butylated hydroxyanisole (BHA), butylated hydroxytoluene (BHT), sodium ascorbate, sodium metabisulfite (SMB), 1-carnosine, propyl gallate (PG), tertiary butyl hydroquinone, cysteine (CYS), citric acid, tartaric acid, phosphoric acid, and ascorbic acid.

In some embodiment of the invention, the amount of antioxidant in the composition/formulation is present in the range of 0.1 to 10% by wt. of the composition/formulation.

In further embodiment, the lubricant is selected from magnesium stearate, zinc stearate, calcium stearate, glycerin monostearate, glyceryl behenate, glyceryl palmitostearate, hydrogenated castor oil, hydrogenated vegetable oil, light mineral oil, magnesium lauryl sulfate, medium-chain triglycerides, mineral oil, myristic acid, palmitic acid, poloxamer, polyethylene glycol, sodium benzoate, sodium chloride, sodium lauryl sulfate, sodium stearyl fumarate, stearic acid, talc, potassium, or sodium benzoate or the like.

In some embodiment of the invention, the amount of lubricant in the composition/formulation is present in the range of 0.1% by wt. to 5.0% by wt. of the total composition/formulation.

In another embodiment, the solubilizing agent is selected from polysorbate 80, sodium lauryl sulfate, anionic emulsifying wax, nonionic emulsifying wax, glyceryl monooleate, phospholipids, polyoxyethylene alkyl ethers, polyoxyethylene castor oil derivatives, polyoxyethylene sorbitan fatty acid esters, polyoxyethylene stearates, polyoxylglycerides, sorbitan esters, triethyl citrate, vitamin E, polyethylene glycol succinate, microcrystalline cellulose, carboxymethylcellulose sodium, diethanolamine, ethylene glycol palmitostearate, glycerin monostearate, hypromellose, hypromellose, acetate succinate, lecithin, polyethylene alkyl ethers, aluminum oxide, poly(methyl vinyl ether/maleic anhydride), calcium carbonate, crospovidone, cyclodextrins, fructose, hydroxypropyl betadex, oleyl alcohol, povidone, benzalkonium chloride, benzethonium chloride, benzyl alcohol, benzyl benzoate, cetylpyridinium chloride, inulin, meglumine, poloxamer, pyrrolidone, sodium bicarbonate, starch, stearic acid, sulfobutylether beta cyclodextrin, tricaprylin, triolein, docusate sodium, glycine, alcohol, self-emulsifying glyceryl monooleate, cationic benzethonium chloride, cetrimide, xanthan gum, lauric acid, myristyl alcohol, butylparaben, ethyl paraben, methylparaben, propylparaben, sorbic acid or the like.

In some embodiment of the invention, the amount of solubilizing agent or surfactant in the composition/formulation of the present invention ranges from 0.1% to 10%, preferably 0.1% to 5.0% by wt. of the composition/formulation.

In some embodiment of the invention, the glidant is selected from colloidal silicon dioxide, magnesium stearate, fumed silica (colloidal silicon dioxide), starch, talc, calcium phosphate tribasic, cellulose powdered, hydrophobic colloidal silica, magnesium oxide, zinc stearate, magnesium silicate, magnesium trisilicate, silicon dioxide or the like.

In some embodiment of the invention, the amount of glidant present in the composition/formulation ranges from 0.1% by wt. to 5.0% by wt. of the total composition/formulation.

In some embodiment of the inventions, the stabilizers are selected from the group consisting of alginate, agar, carrageen, gelatin, guar gum, gum arabic, locust bean gum, pectin, starch, xanthan gum, trehalose and likewise.

In some embodiment of the invention, the amount of stabilizers in the composition/formulation ranges from 0.1% by wt. to 10.0% by wt. of the total composition/formulation.

In some embodiment of the invention, the plasticizers are added to coating formulations selected from the group propylene glycol, glycerol, glyceryl triacetate (triacetin), triethyl citrate, acetyl triethyl citrate, diethyl phthalate, acetylated monoglycerides, castor oil, mineral oil and like thereof.

In some embodiment of the invention, the plasticizer in the composition/formulation is present in a range of 0.1% to 5.0% by weight of the total composition/formulation.

In some embodiment of the invention, the solvent is selected from water, alcohol, isopropyl alcohol, propylene glycol, mineral oil, benzyl alcohol, benzyl benzoate, flavored glycol, carbon dioxide, castor oil, corn oil (maize), cottonseed oil, dimethyl ether, albumin, dimethylacetamide, ethyl acetate, ethyl lactate, medium-chain triglycerides, methyl lactate, olive oil, peanut oil, polyethylene glycol, polyoxyl, castor oil, propylene carbonate, pyrrolidone, safflower oil, sesame oil, soybean oil, sunflower oil, water-miscible solvents, organic polar or non-polar solvents or mixtures thereof.

In some embodiment of the invention, the amount of solvent in the composition/formulation is used in a quantity sufficient to 100% by wt. of the composition/formulation.

The additional additives include polymer, a plasticizer, a sweetener, and a powdered flavor, preservative, colorant, surfactant, and other excipients. The powdered flavor composition includes a flavourant associated with a solid carrier, coating materials are used, for example synthetic polymers, shellac, corn protein (zein) or other polysaccharides, gelatin, fatty acids, waxes, shellac, plastics, and plant fibers and like thereof. The additives are used in the range of 1 to 30% w/w of unit dose.

In another embodiment, the invention provides synergistic nutritional composition comprising exogenous blend of agmatine (AGM) and inosine monophosphate (IMP) and salts thereof along with pharmaceutical excipients, wherein pharmaceutical excipients are a diluent present in the range of 1 to 30%; a binder present in the range of 0.1 to 30%; an antioxidant present in the range of 0.1 to 10%; a lubricant present in the range of 0.1 to 5.0%; a glidant present in the range of 0.1 to 5.0%; an additive present in the range of 1 to 10%; a surfactant present in the range of 0.1 to 5.0%; a stabilizer present in the range of 0.1 to 5.0%; a plasticizer present in a range of 0.1 to 5.0%; by weight of total composition.

In another embodiment, the invention relates to synergistic nutritional composition, which can be prepared in a manner well known in the pharmaceutical art, and can be administered by a variety of routes, depending upon whether local or systemic treatment is desired and upon the area to be treated. The preferable route of administration includes but not limited to sublingual, rectal, topical, parenteral, nasal, or oral.

In some embodiment, the instant synergistic medicinal composition can be administered to the subject in need thereof, in the form which is suitable for oral use, such as a tablet, capsule (in the form of delayed release, extended release, sustained release, enteric coated release); hard gelatin capsules, soft gelatin capsules in an oily vehicle, veg capsule, hard or soft cellulose capsule, granulate for sublingual use, effervescent or carbon tablets, aqueous or oily solution, suspension or emulsion, encapsulate, matrix, coat, beadlets, nanoparticles, caplet, granule, particulate, agglomerate, spansule, chewable tablet, lozenge, troche, solution, suspension, rapidly dissolving film, elixir, gel, tablets, pellets, granules, capsules, lozenges, aqueous or oily solutions, suspensions, emulsions, sprays or reconstituted dry powdered form with a liquid medium or syrup; for topical use including transmucosal and transdermal use, such as a cream, ointment, gel, aqueous or oil solution or suspension, salve, parch or plaster; for nasal use, such as a snuff nasal spray or nasal drops; for vaginal or rectal use, such as a suppository; for administration by inhalation, such as a finely divided powder or a liquid aerosol; for sub-lingual or buccal use, such as a tablet, capsule, film, spray. Further the composition can be formulated for parenteral use including intravenous, subcutaneous, intramuscular, intravascular, infusion, intraperitoneal, intracerebral, intracerebroventricular, or intradermal.

Formulations of the present invention suitable for oral administration can be presented as discrete units such as capsules (e.g., soft-gel capsules), cachets or tablets each containing a predetermined amount of the active ingredient; as a powder or granules; as a solution or a suspension in an aqueous liquid or a non-aqueous liquid, syrup; or as an oil-in-water liquid emulsion or a water-in-oil liquid emulsion.

Further the present composition can be formulated in the form of age-appropriate pediatric oral dosage forms such as syrup, minitablets, chewable formulations, orodispersible films, and orodispersible tablets.

The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose (in single or divided doses) ranges from about 1 mg per day to about 5000 mg per day, preferably about 100 mg per day to about 1500 mg per day.

In some embodiment, the total daily dose can be administered in the range of about 2 mg to about 2000 mg per day, and preferably about 5 mg to about 2000 mg per day.

In another embodiment, an effective unit dose of the present synergistic composition for oral administration is in a range of 5 mg to 1000 mg.

It is further recommended that children, patients over 60 years old, initially receive low doses and that the dosage be titrated based on individual physiological responses and/or pharmacokinetics. It can be necessary to use dosages outside these ranges in some cases, as will be apparent to those in the art. Further, it is noted that the clinician or treating physician knows how and when to interrupt, adjust, or terminate therapy in conjunction with an individual patient's response.

In yet another embodiment, the present stable, synergistic nutritional composition is formulated for infants and adult humans.

The use of any and all examples, or exemplary language (e.g., "such as") provided herein, is intended merely to better illuminate the invention, and does not pose a limitation on the scope of the invention unless otherwise claimed.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

The invention may be further illustrated by the following examples, which are for illustrative purposes only and should not be construed as limiting the scope of the invention in anyway. The present invention is not to be limited in terms of the particular embodiments described in this application, which are intended as single illustrations of individual aspects of the invention. Functionally equivalent compositions and treatments within the scope of the invention, in addition to those enumerated herein, will be apparent to those skilled in the art from the foregoing description and examples. Such modifications and variations are intended to fall within the scope of the appended claims. The contents of each reference, patent and patent application cited in this application is hereby incorporated by reference in its entirety.

EXAMPLES

Having described the basic aspects of the present invention, the following non-limiting examples illustrate specific embodiments thereof. Those skilled in the art will appreciate that many modifications may be made in the invention without changing the essence of invention.

Example-1 i. Composition 1: Synergistic blend

| Ingredient | w/w % |
|---|---|
| Inosine Monophosphate (IMP) | 40%-90% |
| Agmatine Sulphate (AGM) | 10%-55% | ii. Composition 2: Tablet/Capsule

| Ingredient | w/w % unit dose |
|---|---|
| Inosine Monophosphate (IMP) | 60 ± 5% |
| Agmatine Sulphate (AGM) | 30 ± 5% |
| Excipient | 5-10% |
| Average Wt | 100% |
| Average wt in mg | 800-900 mg | iii. Composition 3: Tablet/Capsule

| Ingredient | w/w % unit dose |
|---|---|
| Inosine Monophosphate (IMP) | 65 ± 6% |
| Agmatine Sulphate (AGM) | 25 ± 5% |
| Excipient | 5-20% |
| Average Wt | 100% |
| Average wt in mg | 400-500 mg | v. Composition 4: Tablet/Capsule

| Ingredient | mg per unit dose |
|---|---|
| Inosine Monophosphate (IMP) | 500 |
| Agmatine Sulphate (AGM) | 250 |
| L-Carnosine | 50 |
| Microcrystalline Cellulose | 1-20 |
| Silicon dioxide | 2-15 |
| Hydroxypropyl Methylcellulose | 1-10 |
| Zinc Stearate | 1-10 |
| PVP K-30 | 5-10 |
| Talc | 1-10 |
| Polysorbate 80 | 1-10 |
| Mannitol | 1-20 |
| Propylene Glycol | QS |
| Water | QS |
| Average weight | 800-900 mg | vii. Composition 5: Tablet/Capsule

| Ingredient | mg per unit dose |
| --- | --- |
| Inosine Monophosphate (IMP) | 250 |
| Agmatine Sulphate (AGM) | 100 |
| L-Carnosine | 25 |
| Sodium ascorbate | 1-10 |
| Microcrystalline Cellulose | 2-20 |
| Silicon dioxide | 5-15 |
| Hydroxypropyl Methylcellulose | 2-10 |
| Magnesium Stearate | 2-10 |
| PVP K-30 | 5-10 |
| Talc | 1-10 |
| Polysorbate 80 | 5-20 |
| Mannitol | 5-20 |
| Alcohol | QS |
| Water | QS |
| Average weight | 400-480 mg | viii. Composition 6: Tablet/Capsule

| Ingredient | mg per unit dose |
| --- | --- |
| Inosine Monophosphate (IMP) | 400 |
| Agmatine Sulphate (AGM) | 400 |
| Tocopherol | 1-10 |
| Microcrystalline Cellulose | 2-20 |
| Silicon dioxide | 5-15 |
| Hydroxypropyl Methylcellulose | 2-10 |
| Magnesium Stearate | 2-10 |
| PVP K-30 | 5-10 |
| Talc | 1-10 |
| Polysorbate 80 | 5-20 |
| Mannitol | 5-20 |
| Methylene Chloride | QS |
| Water | QS |
| Average weight | 850-900 mg | ix. Composition 7: Tablet/Capsule

| Ingredient | mg per unit dose |
| --- | --- |
| Inosine Monophosphate (IMP) | 100 |
| Agmatine Sulphate (AGM) | 50 |
| Ascorbic acid | 1-10 |
| Microcrystalline Cellulose | 1-10 |
| Silicon dioxide | 1-10 |
| Hydroxypropyl Methylcellulose | 1-10 |
| Magnesium Stearate | 2-10 |
| PVP K-30 | 5-10 |
| Talc | 1-10 |
| Polysorbate 80 | 5-20 |
| Manitol | 5-20 |
| IPA | QS |
| Water | QS |
| Average weight | 400-500 mg | vii. Composition 8: Tablet/Capsule

| Ingredient | mg per unit dose |
| --- | --- |
| Inosine Monophosphate (IMP) | 300 |
| Agmatine Sulphate (AGM) | 100 |
| Ascorbic acid | 1-10 |
| Microcrystalline Cellulose | 1-10 |
| Silicon dioxide | 1-10 |
| Hydroxypropyl Methylcellulose | 1-10 |
| Magnesium Stearate | 2-10 |
| PVP K-30 | 5-10 |
| Talc | 1-10 |
| Polysorbate 80 | 5-20 |
| Manitol | 5-20 |

| Ingredient | mg per unit dose |
| --- | --- |
| IPA | QS |
| Water | QS |
| Average weight | 400-500 mg | vii. Composition 9: Tablet/Capsule

| Ingredient | mg per unit dose |
| --- | --- |
| Inosine Monophosphate (IMP) | 300 |
| Agmatine Sulphate (AGM) | 150 |
| Ascorbic acid | 1-10 |
| Microcrystalline Cellulose | 1-10 |
| Silicon dioxide | 1-10 |
| Hydroxypropyl Methylcellulose | 1-10 |
| Magnesium Stearate | 2-10 |
| PVP K-30 | 5-10 |
| Talc | 1-10 |
| Polysorbate 80 | 5-20 |
| Manitol | 5-20 |
| IPA | QS |
| Water | QS |
| Average weight | 400-500 mg | vii. Composition 10: Tablet/Capsule

| Ingredient | mg per unit dose |
| --- | --- |
| Inosine Monophosphate (IMP) | 400 |
| Agmatine Sulphate (AGM) | 250 |
| Ascorbic acid | 1-10 |
| Microcrystalline Cellulose | 1-10 |
| Silicon dioxide | 1-10 |
| Hydroxypropyl Methylcellulose | 1-10 |
| Magnesium Stearate | 2-10 |
| PVP K-30 | 5-10 |
| Talc | 1-10 |
| Polysorbate 80 | 5-20 |
| Manitol | 5-20 |
| IPA | QS |
| Water | QS |
| Average weight | 400-500 mg | vii. Composition 11: Tablet/Capsule

| Ingredient | mg per unit dose |
| --- | --- |
| Inosine Monophosphate (IMP) | 500 |
| Agmatine Sulphate (AGM) | 350 |
| Ascorbic acid | 1-10 |
| Microcrystalline Cellulose | 1-10 |
| Silicon dioxide | 1-10 |
| Hydroxypropyl Methylcellulose | 1-10 |
| Magnesium Stearate | 2-10 |
| PVP K-30 | 5-10 |
| Talc | 1-10 |
| Polysorbate 80 | 5-20 |
| Manitol | 5-20 |
| IPA | QS |
| Water | QS |
| Average weight | 400-500 mg | vii. Composition 12: Tablet/Capsule

| Ingredient | mg per unit dose |
| --- | --- |
| Inosine Monophosphate (IMP) | 500 |
| Agmatine Sulphate (AGM) | 400 |
| Ascorbic acid | 1-10 |

-continued

| Ingredient | mg per unit dose |
|---|---|
| Microcrystalline Cellulose | 1-10 |
| Silicon dioxide | 1-10 |
| Hydroxypropyl Methylcellulose | 1-10 |
| Magnesium Stearate | 2-10 |
| PVP K-30 | 5-10 |
| Talc | 1-10 |
| Polysorbate 80 | 5-20 |
| Manitol | 5-20 |
| IPA | QS |
| Water | QS |
| Average weight | 400-500 mg |

Example 2: Animal Study

The purpose of this study is to evaluate the effect of the test substance in Swiss albino rats.

Test System and Animal Husbandry

Species: Mice

Strain: Swiss albino

No. of animals: 30 Animals (5 groups of 6 animals each)

Administration

Group 1 is placebo, Group 2 was given a standard treatment of antithrombotic, antiepileptic, anti-inflammatory and steroid protocol (methylprednisolone) and Group 3, Group 4 and Group 5 served as test substance. Animals were subjected to SCI and outcome measures were monitored.

Group, Designation and Dose Levels:

TABLE 1

Animal grouping and treatment details

| Groups | Group Description | Dose Level | No. of animals |
|---|---|---|---|
| Group 1 | Placebo | Phosphate-buffered saline | 6 |
| Group 2 | Reference standard | 60 mg/kg | 6 |
| Group 3 | Test I [Inosine Monophosphate disodium salt hydrate (IMP)] | 102 mg/kg | 6 |
| Group 4 | Test II [Agmatine Sulphate (AGM)] | 51 mg/kg | 6 |
| Group 5 | Test I + Test II [IMP + AGM] | 102 mg/kg + 51 mg/kg | 6 |

Results:

TABLE 2

No. of fold increase in plasticity proteins from baseline

| Group | Treatment group | GAP-43 | BDNF | NGF | NTF3 |
|---|---|---|---|---|---|
| G1 | Placebo | 1.69 | 1.41 | 1.21 | 1.11 |
| G2 | Reference standard | 5.89 | 3.36 | 4.88 | 2.2 |
| G3 | Test I [Inosine monophosphate disodium salt hydrate (IMP)] | 4.57 | 2.95 | 4.11 | 2.44 |
| G4 | Test II [Agmatine sulphate (AGM)] | 3.44 | 2.44 | 1.69 | 1.17 |
| G5 | Test I + Test II [IMP + AGM] | 11.61 | 7.89 | 6.31 | 3.66 |

TABLE 3

Percentage change in brain ionic Zinc conc.

| Group | Treatment group | % |
|---|---|---|
| G1 | Placebo | 186000% |
| G2 | Reference standard | 30000% |
| G3 | Test I [Inosine monophosphate disodium salt hydrate (IMP)] | 43000% |
| G4 | Test II [Agmatine sulphate (AGM)] | 66000% |
| G5 | Test I + Test II [IMP + AGM] | −98.41% |

TABLE 4

Percentage improvement of limb movements to baseline

| Group | Treatment group | (Baseline as 1) |
|---|---|---|
| G1 | Placebo | 0.25 |
| G2 | Reference standard | 0.55 |
| G3 | Test I [Inosine monophosphate disodium salt hydrate (IMP)] | 0.40 |
| G4 | Test II [Agmatine sulphate (AGM)] | 0.34 |
| G5 | Test I + Test II [IMP + AGM] | 0.92 |

TABLE 5 percentage of subjects with >1000 axons crossing denervated side

| Group | Treatment group | % |
|---|---|---|
| G1 | Placebo | 0% |
| G2 | Reference standard | 33% |
| G3 | Test I [Inosine monophosphate disodium salt hydrate (IMP)] | 29% |
| G4 | Test II [Agmatine sulphate (AGM)] | 18% |
| G5 | Test I + Test II [IMP + AGM] | 83% |

DISCUSSION

Study End Points

Figure 2:
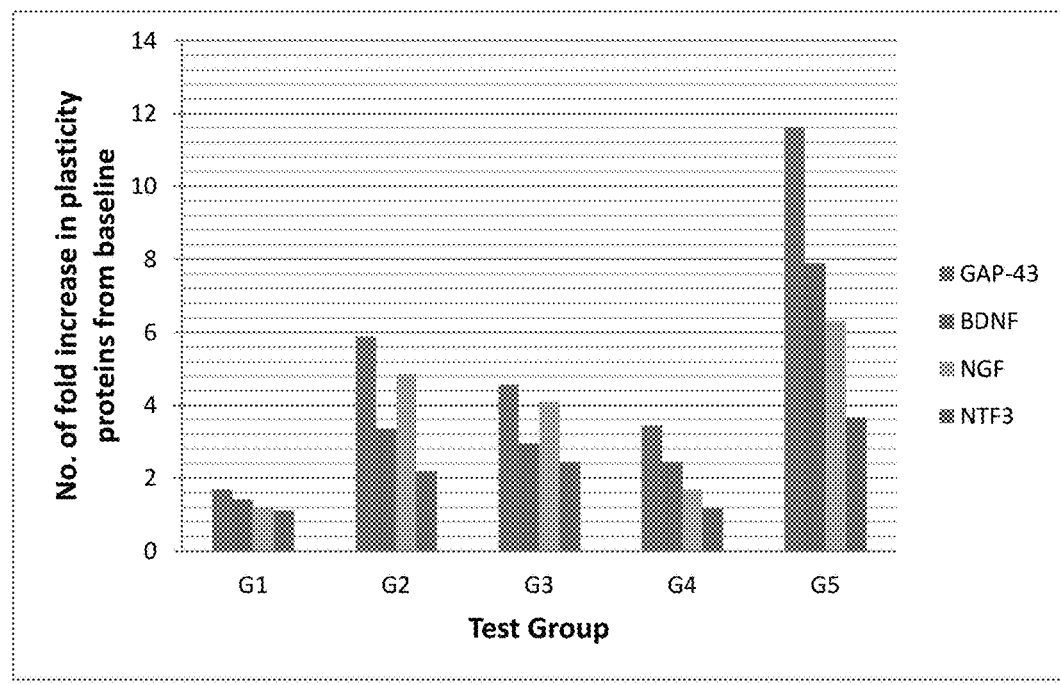
FIG. 2 illustrates No of fold Increase in plasticity proteins from baseline [G1—Placebo; G2—Reference Standard; G3—Test I [IMP salt]; G4—Test II [AGM salt]; G5—Test I+Test II [IMP+AGM]
Figure 3:
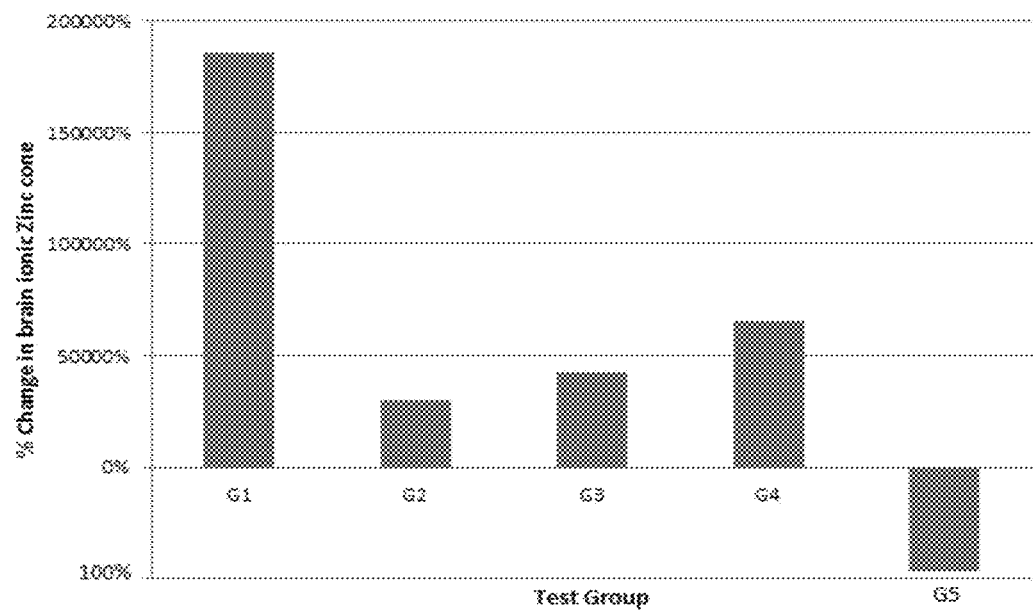
FIG. 3 illustrates Percentage change in ionic zinc2+ concentration in brain [G1—Placebo; G2—Reference Standard; G3—Test I [IMP salt]; G4—Test II [AGM salt]; G5—Test I+Test II [IMP+AGM]
Figure 4:
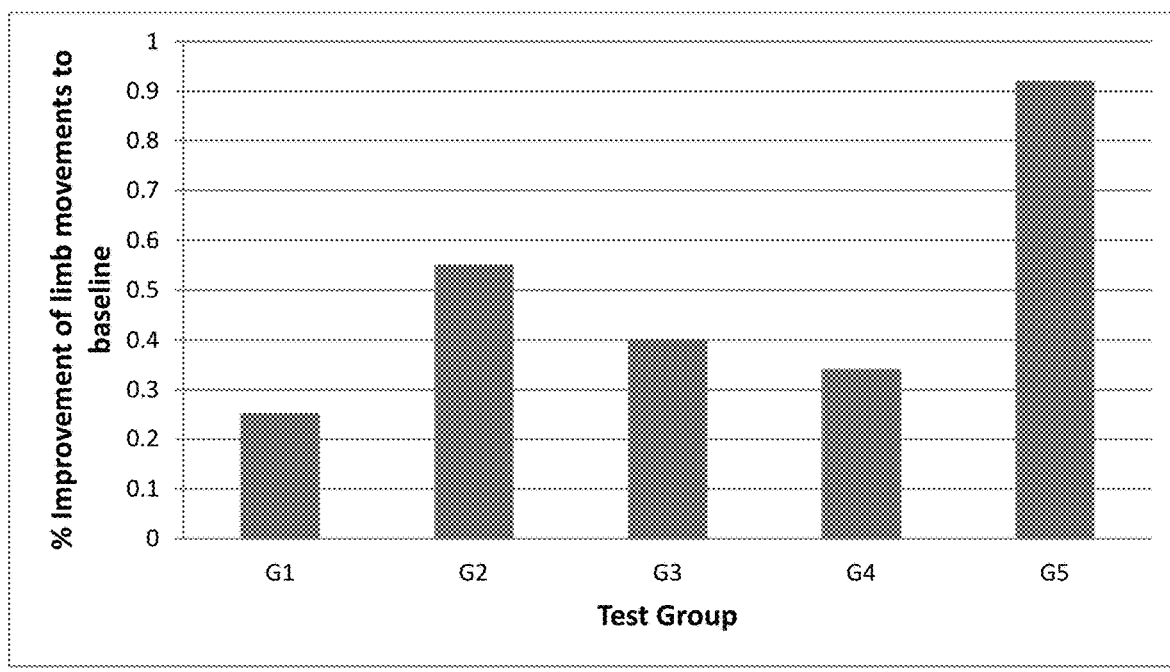
FIG. 4 illustrates Percentage improvement in limb improvements to baseline [G1—Placebo; G2—Reference Standard; G3—Test I [IMP salt]; G4—Test II [AGM salt]; G5—Test I+Test II [IMP+AGM]
Figure 5:
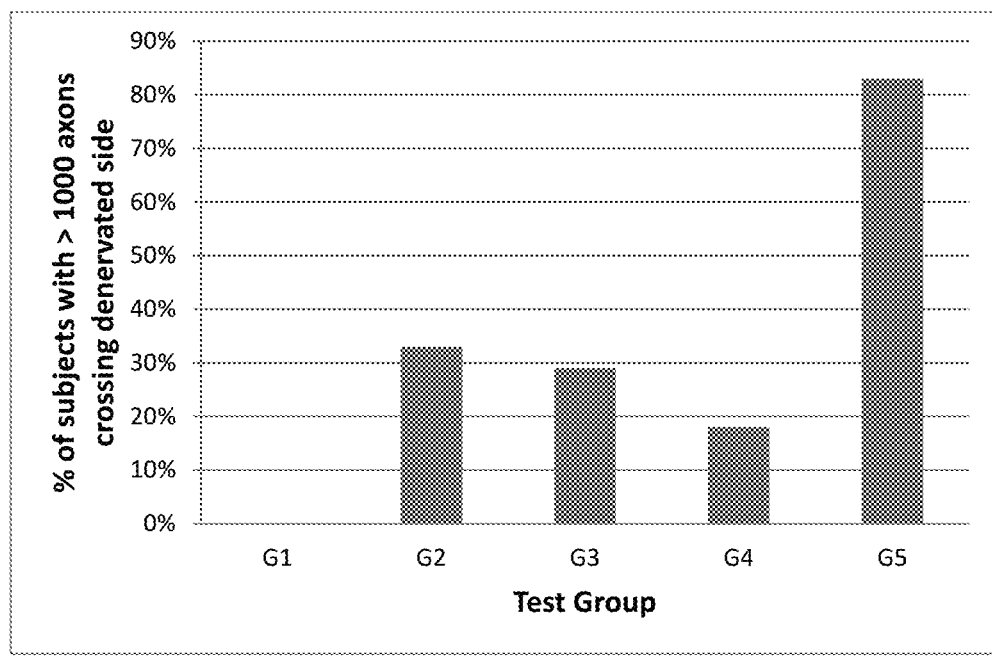
FIG. 5 illustrates of subjects with more than 1000 axon crossing denervated side [G1—Placebo; G2—Reference Standard; G3—Test I [IMP salt]; G4—Test II [AGM salt]; G5—Test I+Test II [IMP+AGM]

1. Increase in plasticity proteins—no. of folds increase from baseline
2. Brain ionic zinc (Zn++)-% change in concentration from baseline
3. Improvement of limb movements—as % to baseline (baseline is '1')
4. Subjects with >1000 axons crossing denervated side—as % subjects Table 2 and FIG. 2 represent the no. of fold increase in plasticity proteins from baseline showing significant increase in the test substances treated group (G5) when compared with Control group (G2), Test substance group (G3) and (G4). Percentage Change in brain ionic Zinc conc were showing significant decrease in the test substances treated group (G5) when compared with Ischemia Reperfusion Control group (G2) (Table 3 & FIG. 3). FIG. 4 represent % Improvement of limb movements to baseline (baseline as 1). FIG. 5 represent % of subjects with >1000 axons crossing denervated side.

CONCLUSION

Arms with Group 5 produces statistically significant results as compared placebo (G1), standard (G2) and individual dose (G3 & G4), treatment arm (p<0.00001). G5 produces significantly superior results over placebo and standard treatment arm and is superior as compared to G3 and G4. There is significantly higher up regulation of plasticity proteins like GAP-43, BDNF, and NGF& NTF 3 ranging from 3-fold to 12-fold from baseline. G5 achieves >98% reduction in CNS ionic Zn++ concentration. Further G5 accomplishes highest improvement in limb movement of 0.92 to baseline (as 1). G5 exhibits superior neuron sprouting and re-wiring effects with >83% subjects with >1000 axons crossing denervated side as compared to 0% with placebo and 33% with standard treatment arm.

We claim:

1. A synergistic nutritional composition for promoting axonal regeneration, the synergistic nutritional composition comprising: a therapeutically effective exogenous combination of a crystalline form of an inosine monophosphate salt and an agmatine salt, wherein the inosine monophosphate salt and the agmatine salt are present in a weight ratio of 1:0.4 to 1:0.8, along with pharmaceutically acceptable excipients wherein the composition is formulated for oral administration.

2. The synergistic nutritional composition as claimed in claim 1, wherein the inosine monophosphate salt is a white crystalline inosine monophosphate disodium salt hydrate.

3. The synergistic nutritional composition as claimed in claim 1, wherein the agmatine salt is a white crystalline agmatine sulphate.

4. The synergistic nutritional composition as claimed in claim 1, wherein the white crystalline inosine monophosphate disodium salt hydrate is present in a range of 40% to 90% by weight of the total composition.

5. The synergistic nutritional composition as claimed in claim 1, wherein the white crystalline agmatine sulphate is present in a range of 10% to 55% by weight of the total composition.

6. The synergistic nutritional composition as claimed in claim 1, wherein the pharmaceutically acceptable excipients are selected from a group consisting of a diluent present in a range of 1 to 30%; a binder present in a range of 0.1 to 30%; an antioxidant present in a range of 0.1 to 10%; a lubricant present in a range of 0.1 to 5.0%; a glidant present in a range of 0.1 to 5.0%; an additive present in a range of 1 to 10%; a surfactant present in a range of 0.1 to 5.0%; a stabilizer present in a range of 0.1 to 5.0%; and a plasticizer present in a range of 0.1 to 5.0%, by weight of the total composition.

7. The synergistic nutritional composition as claimed in claim 1, wherein an effective unit dose of the composition for an oral administration is formulated in a range of 5 mg to 1000 mg.

8. The synergistic nutritional composition as claimed in claim 1, wherein the composition is formulated for infants and adult humans.

9. The synergistic nutritional composition as claimed in claim 1, wherein the synergistic nutritional composition is configured for treating an axonal degeneration disorder, wherein the axonal degeneration disorder is selected from a group consisting of spinal cord injury (SCI), head and spinal cord trauma, haemolytic uremic syndrome, complement mediated kidney disease, ischemia reperfusion disorders, transplant rejection, meningitis, Alzheimer's disease (AD), age-related macular degeneration, multiple sclerosis (MS), Huntington's disease, Parkinson's disease (PD), traumatic brain injury/trauma, Wallerian degeneration (WD), atherosclerosis, coronary heart disease, osteoarthritis, Acute Disseminated Encephalomyelitis (ADEM), amyotrophic lateral sclerosis (ALS), Concentric Sclerosis, Charcot-Marie-Tooth Disease (CMT), Guillain-Barre Syndrome (GBS), Neuromyelitis Optica (Devic's Disease), chronic inflammatory demyelinating neuropathies (CIDP), Schilder's Disease, Transverse Myelitis, distal axonopathies, Idiopathic inflammatory demyelinating diseases, metabolic encephalopathies, acute haemorrhagic leucoencephalitis, leukodystrophies and central pontine myelinolysis, malaria, acquired immunodeficiency syndrome (AIDS) and infection with human lymphotropic virus type 1 (HTLV-I) causing HTLV-I-associated myelopathy (HAM), tropical spastic paraparesis (TSP) and subcortical ischaemic damage, and brain trauma.

10. The synergistic nutritional composition as claimed in claim 1, wherein the composition up-regulates plasticity proteins selected from a group consisting of Growth Associated Protein 43 [GAP-43], Brain-derived neurotrophic factor [BDNF], nerve growth factor [NGF], and Neurotrophin-3 [NTF 3].

11. The synergistic nutritional composition as claimed in claim 10, wherein the composition up-regulates plasticity protein with 3-12 folds from baseline.

12. The synergistic nutritional composition as claimed in claim 1, wherein the composition achieves more than 98% reduction in CNS ionic zinc concentration.

13. The synergistic nutritional composition as claimed in claim 1, wherein the composition exhibits neuron sprouting and re-wiring effects with more than 83% subjects with 1000 axons crossing denervated side.

14. The synergistic nutritional composition as claimed in claim 1, wherein the composition achieves improvement in limb movement of 0.92 to baseline.

* * * * *